United States Patent
Szecsody et al.

(10) Patent No.: US 6,438,501 B1
(45) Date of Patent: Aug. 20, 2002

(54) FLOW THROUGH ELECTRODE WITH AUTOMATED CALIBRATION

(75) Inventors: James E. Szecsody; Mark D. Williams; Vince R. Vermeul, all of Richland, WA (US)

(73) Assignee: Battele Memorial Institute, Richland, WA (US)

( * ) Notice: Subject to any disclaimer, the term of this patent is extended or adjusted under 35 U.S.C. 154(b) by 0 days.

(21) Appl. No.: 09/222,487

(22) Filed: Dec. 28, 1998

(51) Int. Cl.[7] .............................. G01F 1/12; G01F 1/50
(52) U.S. Cl. ........................ 702/100; 702/50; 73/1.03
(58) Field of Search ..................... 702/22–25, 30–32, 702/45, 50, 85, 86, 100, 182, 183, 188, 189; 73/1.02, 1.03; 700/266, 267; 422/82.05, 82.04, 98; 204/401, 406, 409

(56) References Cited

U.S. PATENT DOCUMENTS

| | | | | |
|---|---|---|---|---|
| 3,619,381 A | * | 11/1971 | Fitterer | 205/783.5 |
| 3,889,255 A | * | 6/1975 | Pettersen | 341/120 |
| 4,119,406 A | * | 10/1978 | Clemens | 422/81 |
| 4,384,925 A | * | 5/1983 | Stetter et al. | 205/785.5 |
| 4,499,377 A | * | 2/1985 | Presser | 250/343 |
| 4,713,772 A | * | 12/1987 | Carlson | 702/30 |
| 4,895,618 A | * | 1/1990 | Tikka et al. | 162/49 |
| 4,912,417 A | * | 3/1990 | Gibboney et al. | 324/438 |
| 4,929,314 A | * | 5/1990 | Simonson, III et al. | 205/788 |
| 5,511,408 A | * | 4/1996 | Yoshioka et al. | 73/1.03 |
| 5,739,422 A | * | 4/1998 | Riviello et al. | 73/61.55 |
| 5,801,820 A | * | 9/1998 | Bysouth et al. | 356/36 |
| 5,873,997 A | * | 2/1999 | Kaplan | 210/150 |

* cited by examiner

Primary Examiner—Marc S. Hoff
Assistant Examiner—Manuel L. Barbee
(74) Attorney, Agent, or Firm—Woodard, Emhardt, Naughton, Moriarty & McNett

(57) ABSTRACT

The present invention is an improved automated flow through electrode liquid monitoring system. The automated system has a sample inlet to a sample pump, a sample outlet from the sample pump to at least one flow through electrode with a waste port. At least one computer controls the sample pump and records data from the at least one flow through electrode for a liquid sample. The improvement relies upon (a) at least one source of a calibration sample connected to (b) an injection valve connected to said sample outlet and connected to said source, said injection valve further connected to said at least one flow through electrode, wherein said injection valve is controlled by said computer to select between said liquid sample or said calibration sample. Advantages include improved accuracy because of more frequent calibrations, no additional labor for calibration, no need to remove the flow through electrode(s), and minimal interruption of sampling.

27 Claims, 5 Drawing Sheets

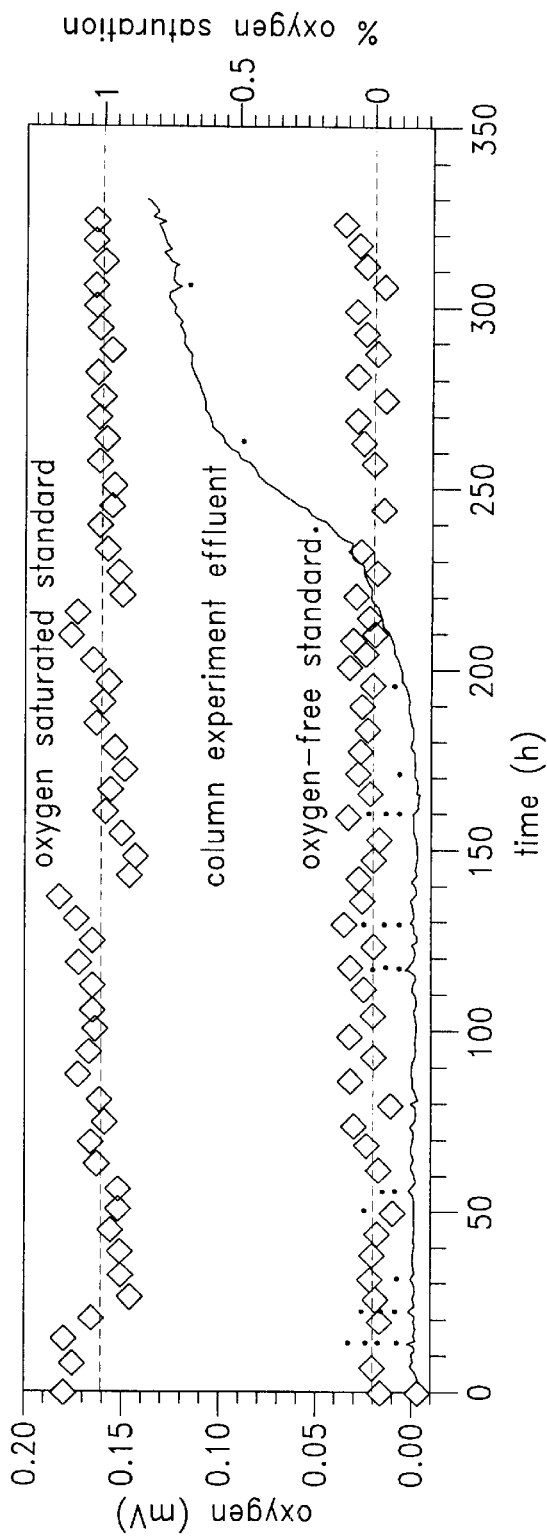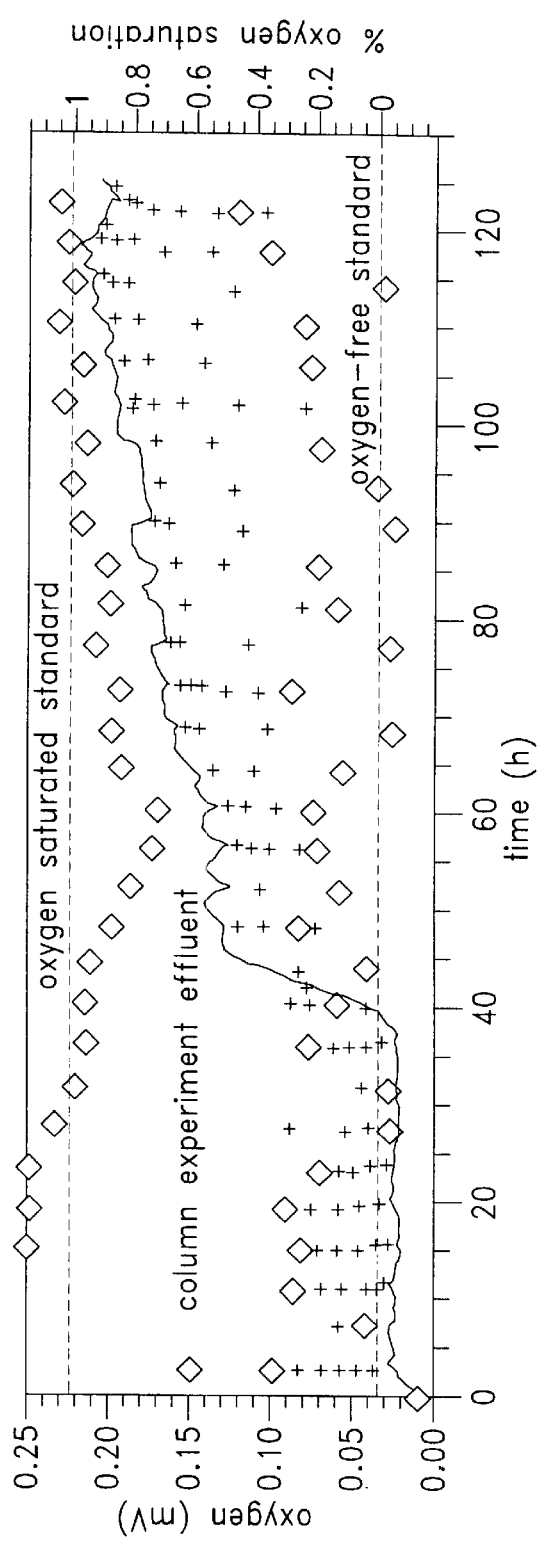

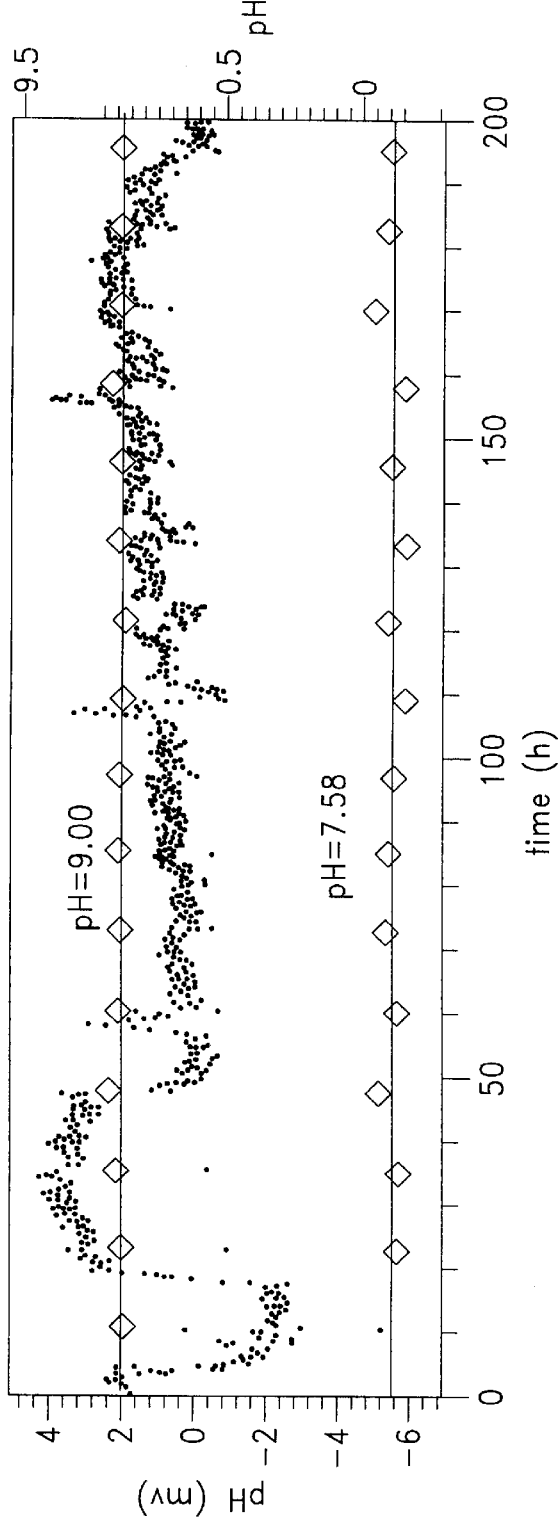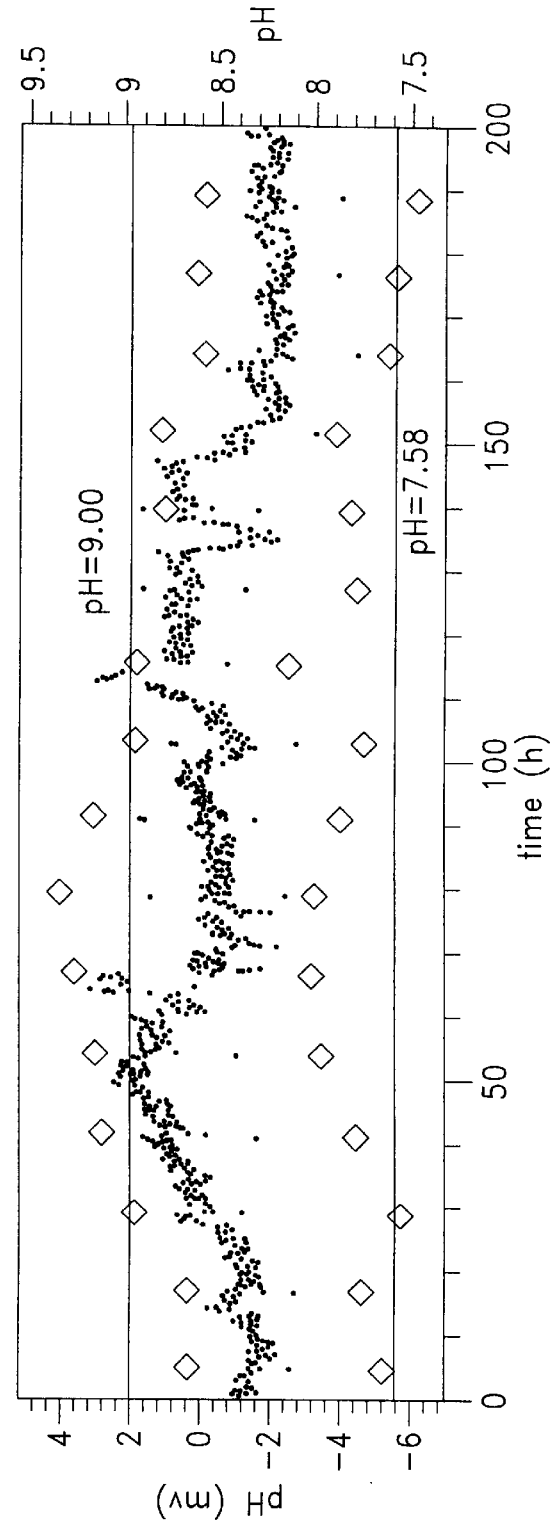

FLOW THROUGH ELECTRODE WITH AUTOMATED CALIBRATION

This invention was made with Government support under Contract DE-AC0676RLO1830 awarded by the U.S. Department of Energy. The Government has certain rights in the invention.

FIELD OF THE INVENTION

The present invention relates to use of one or more flow through electrodes with automated calibration.

As used herein, the term "flow through electrode" includes electrodes used for measuring characteristics or constituents in aqueous solutions including pH, electrical conductivity, dissolved oxygen, specific ion(s) and combinations thereof. The term "flow through electrode" is interchangeable with the term "insertion electrode".

BACKGROUND OF THE INVENTION

Flow through electrodes are used extensively for monitoring industrial processes as well as geochemical conditions of surface water and/or ground water. Operation of flow through electrodes or insertion electrodes always requires calibration to insure accurate measurements are collected from the sample aqueous solution. For periodic measurements or short term studies, manual calibration and measurement of the sample liquid is satisfactory. However, surface water and/or groundwater are extensively monitored at remote locations over long periods of time wherein manual calibration is so labor intensive and/or costly that it is scheduled infrequently and merely assumed to be correct between calibrations.

In FIG. 1 (prior art) an automated monitoring system 100 has a sample inlet 102 directed to at least one flow through electrode(s) 104 with an effluent or waste port 106. At least one computer 108 controls the sample flow and records data from the at least one flow through electrode(s) 104 for a liquid sample. In addition, it is known that a multi-port valve 110 may be used to introduce various liquid samples through the electrode(s) 104. Further, the sample inlet 102 may include a pump 111 for metering the sample. A disadvantage of these prior art systems 100 is the difficulty of calibration of the electrode(s) 104. For calibration, the entire monitoring system 100 must be removed from sample flow and the electrode(s) 104 manually disconnected from the tubing 112. The electrode(s) 104 is/are calibrated by exposure to calibration solutions. In addition to interrupting sampling, significant labor is required for calibration. For certain electrode(s) 104 sensitive to pressure and/or flow rate additional care (labor, time) is needed to match test conditions for an accurate calibration.

Thus, there is a need in the art of flow through electrode monitoring for an improved automated monitoring apparatus with an automated calibration capability.

SUMMARY OF THE INVENTION

The present invention is an improved automated flow through electrode liquid monitoring system. The automated system has a sample inlet to at least one flow through electrode with a waste port. At least one computer controls the sample pump and records data from the at least one flow through electrode for a liquid sample. The improvement relies upon (a) at least one source of a calibration solution; connected to (b) an injection valve connected to the sample inlet and connected to said calibration source, the injection valve further connected to the at least one flow through electrode, wherein the injection valve is controlled by the computer to select between the liquid sample or the calibration sample.

Advantages include diverting sample flow rather than interrupting sample flow, improved accuracy because of more frequent calibrations, capability of matching test conditions of flow rate and/or pressure, capability of multi-point calibrations, no additional labor for calibration, and no need to remove the flow through electrode(s) for calibration.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWINGS

FIG. 4a is a graph of dissolved oxygen versus time for an effluent sample with automated calibration every 12 hours for a stable flow through electrode.

FIG. 4b is a graph of dissolved oxygen versus time for an effluent sample with automated calibration every 12 hours for an unstable flow through electrode.

FIG. 5a is a graph of pH versus time for an effluent sample with automated calibration every 12 hours for a stable flow through electrode.

FIG. 5b is a graph of pH versus time for an effluent sample with automated calibration every 12 hours for an unstable flow through electrode.

DESCRIPTION OF THE PREFERRED EMBODIMENT(S)

Figure 1:
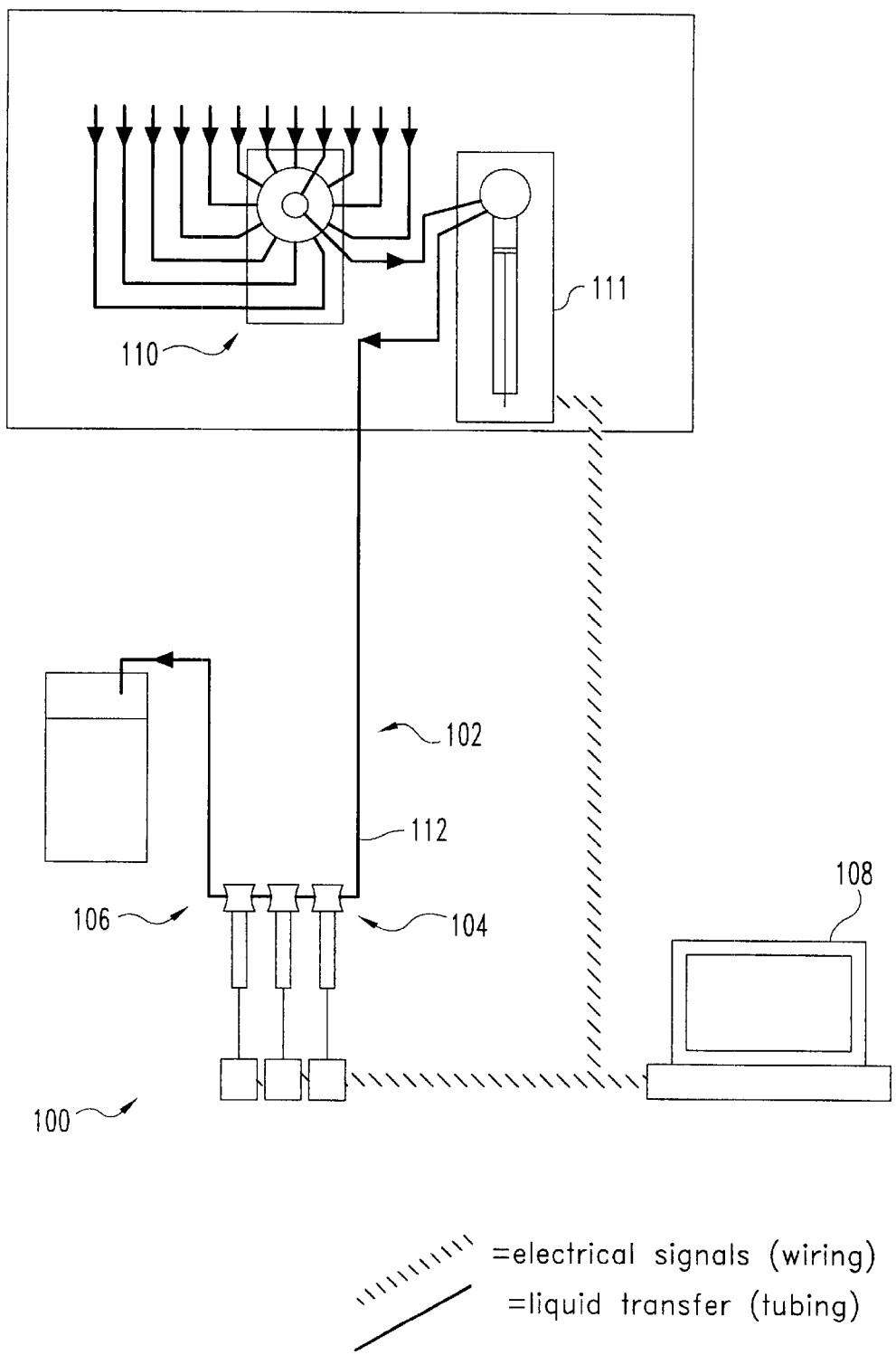
FIG. 1 is a schematic of a prior art flow through sampling system.
Figure 2:
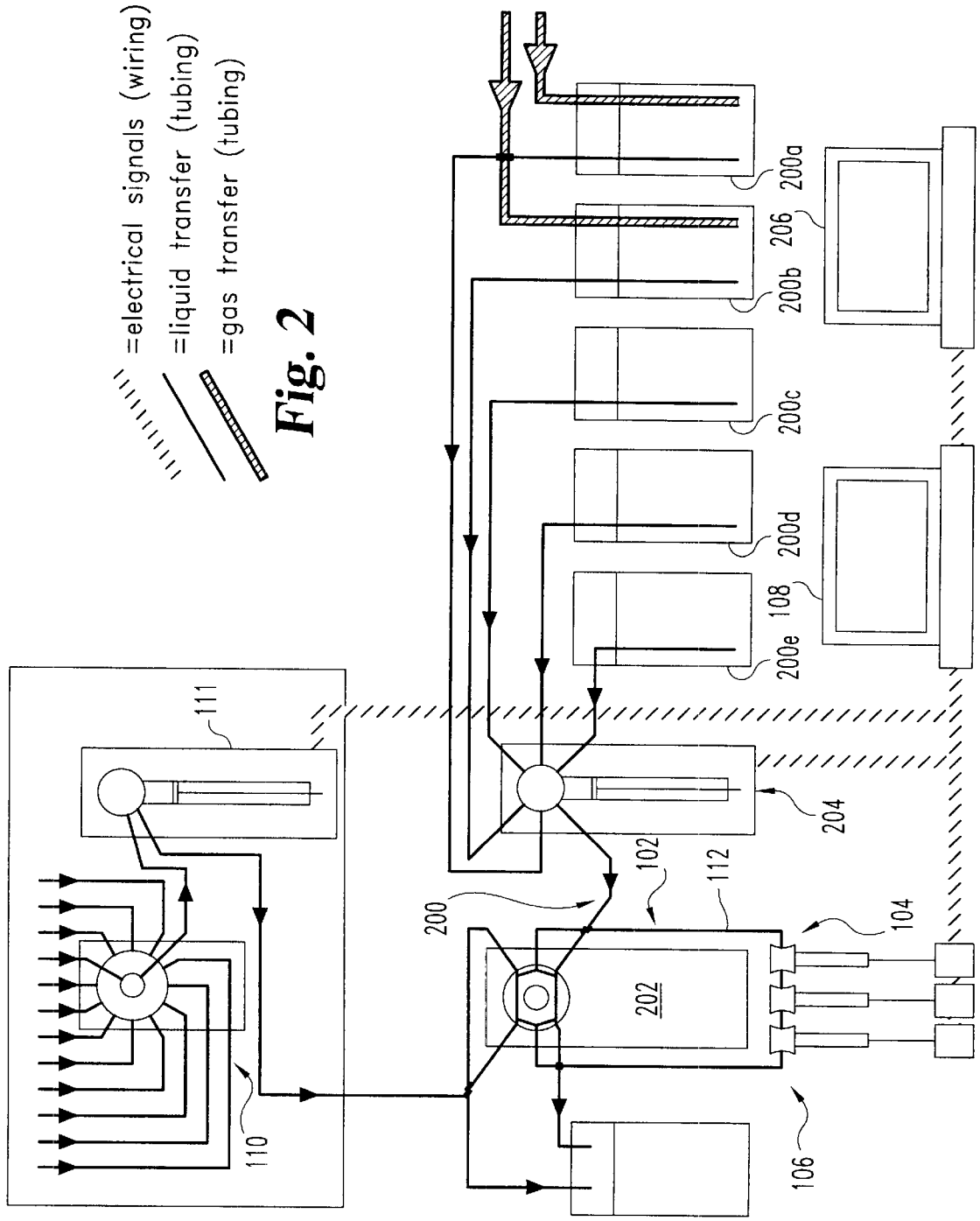
FIG. 2 is a schematic of the flow through sampling system with automated calibration according to the present invention.

The present invention is shown in FIG. 2. The sample inlet 102, flow through electrode(s) 104, computer 108, and tubing 112 are as in FIG. 1. In its most general form, the improvement is based upon (a) at least one source 200 of a calibration solution; connected to (b) an injection valve 202 connected to the sample inlet 102 and the injection valve 202 further connected to the at least one flow through electrode 104, wherein the injection valve 202 is controlled by the computer 108 to select between the liquid sample or the calibration solution. The source may include a calibration pump 204 for passing the calibration solution to the at least one flow through electrode 104. The source may further include a plurality of calibration solution vessels 200a, 200b, 200c, 200d, 200e connected to said calibration pump 204.

To the extent that pump 111, 204 and injection valve 202 operation, and data collection may be specialized, a second computer 206 may be used to separate these functions. The pumps 111, 204 may be any accurately controllable low volume pump and is preferably a syringe pump as may be obtained from Kloehn Company, Ltd., Las Vegas, Nev. The injection valve 202 may be any injection valve, and is preferably a 6-port injection valve, for example as obtained from Valco Instruments Co., Inc., Houston Tex.

The number of calibration vessels 200a–e and the compositions of the calibration liquids depends upon the type of flow through electrode(s) 104 used. If only one flow through electrode 104 is used, only a corresponding calibration solution(s) is/are needed. For example, for calibrating a dissolved oxygen sensor 104, two gas sparged calibration vessels 200a, 200b would be needed. The first calibration vessel 200a may be sparged with air or oxygen to achieve an oxygen saturated calibration liquid, and the second calibration vessel 200b may be sparged with an inert gas, for example helium, to achieve an oxygen free calibration liquid. Similarly, for a pH sensor, or electrical conductive sensor, several calibration vessels 200c, 200d, 200e may be needed for multi-point calibrations. Solutions may be combined when two or more flow through electrodes 104 are used.

The pumps 111, 204 are preferably operated at the same flow rate for most accurate calibrations.

In a preferred embodiment, the second computer 206 contains an analog-to-digital data collection board and collects data from at least one flow through electrode 104. Rate of data collection is variable, preferably about 10 data points per second. The data are integrated over a specified time period and a single value per flow through electrode 104 for the specified time period is recorded to disk with the time period. Calibration data is recorded in data files separate from sample data files on the disk. At preset time intervals, the program on the syringe pump computer 108 that controls the syringe pump 204 and multi-port valve 202 sends a signal to the data logging computer 206 to turn off the sample logging and turn on calibration logging. Calibration and/or sample data may be displayed graphically during operation. A single computer 108 may be used for both pump and valve control and data collection by using an analog-to-digital data collection board mounted in an external box (serial connection) and a multitasking operating system, for example Windows-NT.

EXPERIMENTAL APPARATUS

The present invention has been tested in approximately 60 laboratory experiments that ranged from 100 to 400 hours in length and in 3 field-scale experiments at remote locations. Data from some of the laboratory experiments are shown herein to demonstrate the present invention.

The liquid sampling system as described above was constructed as shown in FIG. 2. One computer (108) was used to automatically control all fluid operations for calibration. This computer (108) was a 25 MHz 80386 computer (16 Mbyte RAM, 250 Mbyte hard drive) portable. A second computer 206 was used in all examples to record laboratory effluent and calibration data. This second computer 206 was a 75 Mhz 80486 computer (16 Mbyte RAM, 350 Mbyte hard drive) which contained an 8 analog, 12 digital input data logging board model #ACJR-12-8 from Strawberry Tree Incorporated, Sunnyvale, Calif. running data logging software Workbench PC, version 2.4.1 (also from Strawberry Tree Incorporated).

In all three examples, the repeated calibration by the automated system provided enough data to determine whether the in line electrodes were properly working and thereby determine the quality of the column data. Manual calibrations would likely not be done as often nor likely be conducted as accurately as the automated system, so the quality of the data without the automated system would be questionable or compromised.

Example 1

Electrical conductivity data was obtained from two laboratory column experiments in which ground water was passed through a sediment column and the electrical conductivity of the effluent ground water was measured. The electrical conductivity electrode was a model #db-5 obtained from Dionex Corporation, Sunnyvale, Calif.

Two calibration vessels were filled with: a) a 130 microsiemen (mS) electrical conductivity solution, b) a 240 mS electrical conductivity solution for two-point electrical conductivity calibration.

Figure 3A:
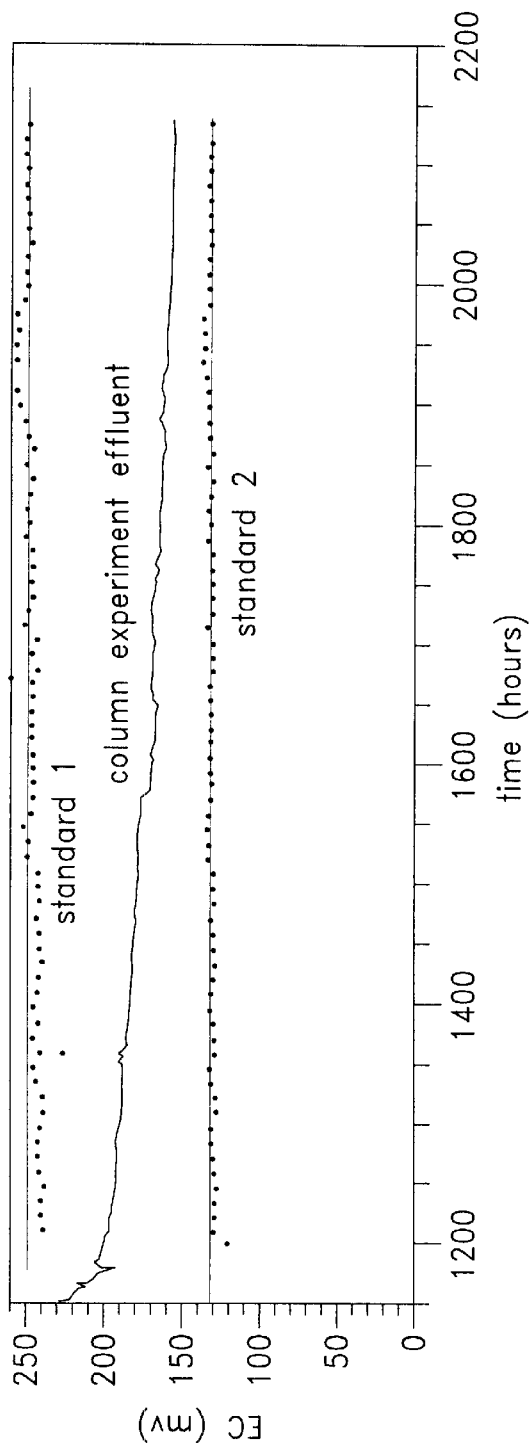
FIG. 3a is a graph of electrical conductivity versus time for an effluent sample with automated calibration every 12 hours for a stable flow through electrode.
Figure 3B:
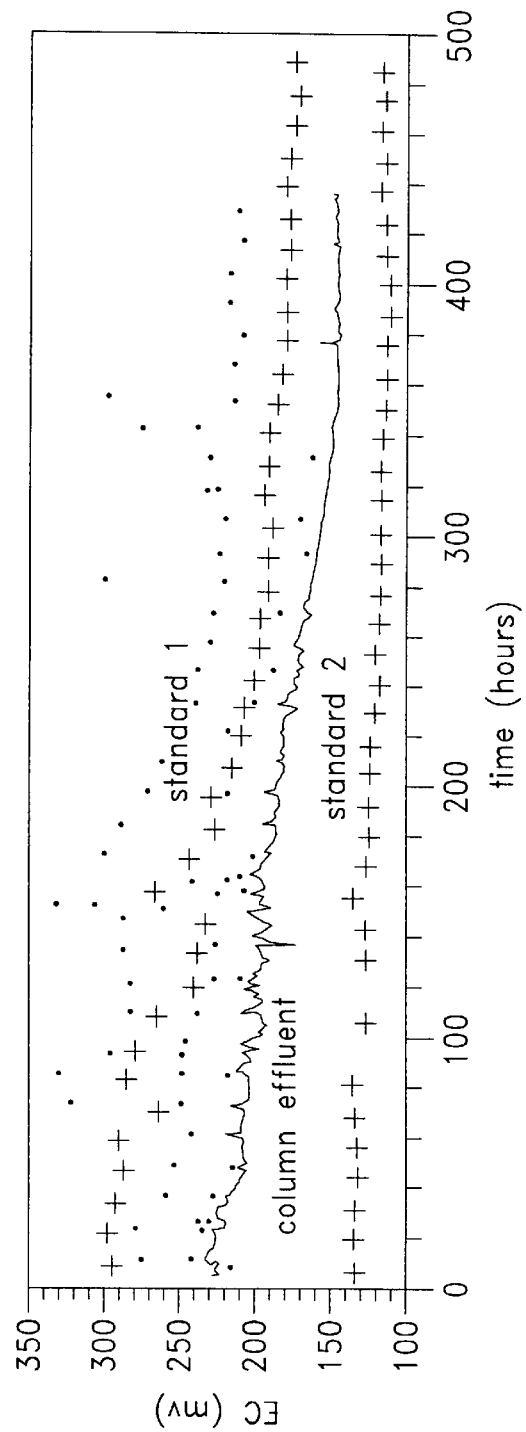
FIG. 3b is a graph of electrical conductivity versus time for an effluent sample with automated calibration every 12 hours for an unstable flow through electrode.

Results for electrical conductivity measurements are shown in FIGS. 3a, and 3b. Automated 2-point calibration (200d, 200e) was done every 12 hours for accuracy verification over the 500 to 1000 h experiments. The electrical conductivity of the column effluent showed a downward trend over time (i.e., the electrical conductivity decreased from 225 mV to 150 mV). The trend in the effluent data is real in one experiment (FIG. 3a) because the calibration data shows that the electrical conductivity in-line electrode had stable response. In contrast, the trend is not real in another experiment (FIG. 3b), because the calibration data shows that the in line electrode response is changing over time. Without the repeated calibration data every 12 hours, it would not be possible to determine that one trend (FIG. 3a) was real and the other (FIG. 3b) was not.

Example 2

Dissolved oxygen data was obtained from two laboratory column experiments wherein oxygen saturated water was passed through a reactive sediment column and the dissolved oxygen of the effluent water was being measured. The dissolved oxygen electrode was a model #16-730 obtained from Microelectrodes, Inc., Londonderry, N.H.

Two calibration vessels were filled with: a) oxygen-free deionized water, and b) oxygen-saturated deionized water. In this example the term "oxygen-saturated" means having an oxygen concentration in equilibrium with atmospheric air. Automated 2-point calibration with oxygen saturated and oxygen free was done every 4 hours over the 130 to 350 hour experiments to verify accuracy.

Results for dissolved oxygen measurements are shown in FIGS. 4a and 4b. The dissolved oxygen of the column effluents both show an upward trend over time (i.e., dissolved oxygen increases from oxygen free to near oxygen saturation). The trend in the effluent data is real in the first example (FIG. 4a) because the calibration data shows the standards are stable within 2.5% over the entire experiment. The trend in the second example (FIG. 4b) may or may not be real, as indicated by the unstable response of calibration standards (calibration data is ±20%). In both examples, the repeated calibration by the automated system provided enough data to determine if the in line electrodes were properly working and then determine the quality of the column data. Manual calibrations would likely not be done as often or could they be conducted as accurately as the automated system, so the quality of the data would be less.

Example 3

Acidity (pH) data was obtained from two laboratory column experiments in which ground water was passed through a sediment column and the pH of the effluent ground water was measured. The pH electrode Corning flat surface pH electrode model #476326 obtained from Fisher Scientific, Pittsburgh, Pa. Two calibration vessels were filled with: a) pH 9.00 solution, b) pH 7.58 solution for two-point calibration near the pH of the effluent water.

Results for pH measurements are shown in FIGS. 5a, and 5b. Automated 2-point calibration (200d, 200e) was done every 12 hours for accuracy verification over the 200 h experiments. The pH of the column effluent showed an increase then decrease over time in both experiments. The trend in the effluent data is real in one experiment (FIG. 6a) because the calibration data shows that the pH in-line electrode had stable response. In contrast, the trend is entirely caused by electrode drift and not real in another experiment (FIG. 5b), because the calibration data increases then decreases over time. Without the repeated calibration data every 12 hours, it would not be possible to determine that one trend (FIG. 5a) was real and the other (FIG. 5b) was not.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An improved automated flow through electrode liquid monitoring system having a sample inlet to at least one flow through electrode with a waste port, in combination with at least one computer for controlling a sample pump and for recording data from said at least one flow through electrode for a liquid sample; wherein the improvement comprises:

(a) at least one source of a calibration solution; connected to (b) an injection valve connected to said sample inlet; said injection valve further connected to said at least one flow through electrode, wherein said injection valve is controlled by said computer to select between said liquid sample or said calibration solution.

2. The system as recited in claim 1, wherein said source includes a calibration pump for receiving said calibration sample and passing said calibration sample to said at least one flow through electrode.

3. The system as recited in claim 1, wherein said calibration solution is oxygen saturated.

4. The system as recited in claim 1, wherein said calibration solution is oxygen-free.

5. The system as recited in claim 1, wherein said calibration solution has a specified pH.

6. The system as recited in claim 1, wherein said calibration solution has a specified electrical conductivity.

7. The system as recited in claim 1, wherein said at least one computer is connected to an analog-to-digital data collection board.

8. The system as recited in claim 7, wherein said at least one computer has a multitasking operating system.

9. The system as recited in claim 1, wherein said at least one computer is two computers.

10. The system as recited in claim 1, further comprising a multi-port valve connected to said sample inlet for introduction of various samples.

11. The system as recited in claim 1, wherein said sample pump is a syringe pump.

12. The system as recited in claim 1, wherein said source includes a syringe pump.

13. The system of claim 1 wherein said at least one source of a calibration solution includes a multi-port valve connected to a plurality of calibration solutions.

14. A fluid monitoring system comprising:

at least one flow through electrode for a liquid sample having a sample inlet and a waste port, at least one computer for controlling a sample pump and for recording data from said at least one flow through electrode, at least one source of a calibration solution, and an injection valve connected to said sample inlet and said waste port of said flow through electrode and to said at least one source of a calibration solution, wherein said injection valve is controlled by said at least one computer to select between delivery of said liquid sample or said calibration solution to said flow through electrode.

15. The system as recited in claim 14, wherein said source includes a calibration pump for receiving said calibration sample and passing said calibration sample to said at least one flow through electrode.

16. The system as recited in claim 14, wherein said calibration solution is oxygen saturated.

17. The system as recited in claim 14, wherein said calibration solution is oxygen-free.

18. The system as recited in claim 14, wherein said calibration solution has a specified pH.

19. The system as recited in claim 14, wherein said calibration solution has a specified electrical conductivity.

20. The system as recited in claim 14, wherein said at least one computer is connected to an analog-to-digital data collection board.

21. The system as recited in claim 20, wherein said at least one computer has a multitasking operating system.

22. The system as recited in claim 14, wherein said at least one computer is two computers.

23. The system as recited in claim 14, further comprising a multi-port valve connected to said sample inlet for introduction of various samples.

24. The system as recited in claim 14, wherein said sample pump is a syringe pump.

25. The system as recited in claim 14, wherein said source includes a syringe pump.

26. The system as recited in claim 14, wherein said injection valve is connected to said sample inlet and said waste port of said flow through electrode.

27. The system of claim 14 wherein said at least one source of a calibration solution includes a multi-port valve connected to a plurality of calibration solutions.

* * * * *